United States Patent
Rostalski et al.

(10) Patent No.: US 9,783,772 B2
(45) Date of Patent: Oct. 10, 2017

(54) CONTROL OF BIOGAS PLANTS

(71) Applicant: KSB Aktiengesellschaft, Frankenthal (DE)

(72) Inventors: Kai Rostalski, Merseburg (DE); Peer Springer, Neuhofen (DE)

(73) Assignee: KSB Akteingesellschaft, Frankenthal (DE)

(*) Notice: Subject to any disclaimer, the term of this patent is extended or adjusted under 35 U.S.C. 154(b) by 0 days.

(21) Appl. No.: 13/632,553

(22) Filed: Oct. 1, 2012

(65) Prior Publication Data
US 2013/0029315 A1  Jan. 31, 2013

Related U.S. Application Data

(63) Continuation of application No. PCT/EP2011/054909, filed on Mar. 30, 2011.

(30) Foreign Application Priority Data

Apr. 1, 2010  (DE) .......................... 10 2010 014 240

(51) Int. Cl.
*C12Q 3/00* (2006.01)
*C12M 1/36* (2006.01)
(Continued)

(52) U.S. Cl.
CPC ............ *C12M 27/06* (2013.01); *C12M 21/04* (2013.01); *C12M 41/42* (2013.01); *Y02E 50/343* (2013.01); *Y02P 20/582* (2015.11)

(58) Field of Classification Search
CPC ...... C12M 21/04; C12M 41/42; C12M 27/06; Y02E 50/343; A21C 1/02; B01F 7/1605;
(Continued)

(56) References Cited

U.S. PATENT DOCUMENTS 7,426,852 B1* 9/2008 Rothman ............. G01N 29/024
                                                702/54
2005/0237852 A1* 10/2005 Chandran .................... 366/136
(Continued)

FOREIGN PATENT DOCUMENTS

DE    40 28 037 A1    3/1992
DE    199 47 339 A1   4/2001
(Continued)

OTHER PUBLICATIONS

English Translation of DE102007063091 acquired from Espacenet Mar. 2013.*

(Continued)

*Primary Examiner* — William H Beisner
*Assistant Examiner* — Danielle Henkel
(74) *Attorney, Agent, or Firm* — Crowell & Moring LLP

(57) ABSTRACT

A method and an apparatus for producing biogas from organic matter including a container (1) which is charged with fermentation substrate by a delivery system (13). At least one stirring mechanism (2) is arranged in the container. The feedback value of at least one measurable variable is detected and transmitted to a control unit (4). A reference variable is also provided to the control unit. The control unit calculates the deviation of the feedback value from the reference value, and actuating variables which modify the power input of the stirring mechanism and/or the composition of the container contents and/or the flow behavior of the container contents are adjusted as a function of the deviation.

16 Claims, 2 Drawing Sheets

(51) Int. Cl.
*C12M 1/06* (2006.01)
*C12M 1/107* (2006.01)
*C12M 1/34* (2006.01)

(58) Field of Classification Search
CPC ............ B01F 15/00155; B01F 15/0229; B01F 15/00344; B01F 15/00376; B01F 15/00246
USPC ...................................... 435/3, 286.5, 286.7
See application file for complete search history.

(56) References Cited

U.S. PATENT DOCUMENTS

| | | | |
|---|---|---|---|
| 2009/0107196 A1* | 4/2009 | Jung | B01F 7/00116 71/59 |
| 2009/0311378 A1* | 12/2009 | Wilaschin | A23C 9/1223 426/43 |
| 2011/0036779 A1* | 2/2011 | Bias et al. | 210/703 |
| 2012/0009664 A1* | 1/2012 | Buerger | 435/286.5 |

FOREIGN PATENT DOCUMENTS

| | | |
|---|---|---|
| DE | 100 56 338 A1 | 6/2001 |
| DE | 10 2005 057 979 A1 | 6/2007 |
| DE | 20 2007 002 835 U1 | 8/2007 |
| DE | 10 2007 063 091 A1 | 7/2009 |
| EP | 0 516 895 A1 | 12/1992 |
| EP | 1 762 607 A1 | 3/2007 |
| WO | WO 2008/104320 A2 | 9/2008 |

OTHER PUBLICATIONS

Machine Translation of EP 0474325 corresponding to DE4028037, accessed Oct. 2013.*
English-language translation of the International Preliminary Report on Patentability dated Oct. 11, 2012. (Six (6) pages).
International Search Report dated Jul. 8, 2011 with English translation (Five (5) pages).
Form PCT/ISA/237 (Four (4) pages).
German Office Action dated Nov. 12, 2010 (Four (4) pages).

* cited by examiner

CONTROL OF BIOGAS PLANTS

CROSS REFERENCE TO RELATED APPLICATIONS

This application is a continuation of international patent application No. PCT/EP2011/054909, filed Mar. 30, 2011 designating the United States of America and published in German on Oct. 6, 2012 as WO 2011/121022, the entire disclosure of which is incorporated herein by reference. Priority is claimed based on Federal Republic of Germany patent application no. DE 10 2010 014 240.9, filed Apr. 1, 2010, the entire disclosure of which is likewise incorporated herein by reference.

BACKGROUND OF THE INVENTION

The invention relates to a method and an apparatus for producing biogas from organic substances, substrate being supplied to a container by a feed system and there being arranged in the container at least one agitator mechanism.

The method serves for generating biogas from organic substances. The raw substance used in such plants for generating biogas is designated as substrate. The substrate is composed of biologically degradable biomass, such as liquid manure, silage or biowaste. The containers used for the production of biogas are also designated as bioreactors or fermenters. When the biogas plants are being operated continuously, substrate is supplied continuously to the container and biogas and also fermentation residue are extracted. Substrate located in the container is converted by means of various types of microorganisms. This biomass to be converted is designated as fermentation substrate. Microbial breakdown gives rise from the fermentation substrate to methane and carbon dioxide as the main components of the biogas.

The substrate supplied is mixed with the container contents. The substrate is supplied mostly by punctiform feed with the aid of fodder systems. The biomass dwell time required for as high a biogas yield as possible is dependent critically upon the mixing of the substrate with the fermentation substrate. In the case of those media which are characterized predominantly by increased viscosities, circulation of the container contents is necessary for mixing and/or intermixing, this taking place, as a rule, by means of agitator mechanisms.

In the sector of anaerobic bioreaction technology, fermenters with a height to diameter ratio greater than 0.5 are used in many applications. Mixing is in this case carried out mostly by means of vertical agitator mechanisms. The agitator mechanism propellers are in this case located on a central shaft driven from outside. The drive shaft is arranged vertically and projects into the container from above, while it mostly runs parallel to the container walls. Such a fermenter is known, for example, from German patent publication no. DE 199 47 339 A1.

Instead, the method according to the invention for producing biogas employs container forms, of which the height to diameter ratio is lower than 0.5. The diameter of the containers preferably lies between 16 and 40 meters. With these container dimensions, it is no longer economically viable to use a central vertical agitator mechanism driven from outside. For mixing the container contents, use is made of agitator mechanisms which are arranged predominantly in the marginal zone of the container and in the latter and which generate mostly horizontal flow of the medium in the container. Such an arrangement is known, for example, from US patent publication No. US 1012/0009664 (=WO 2008/104320).

German utility model No. DE 20 2007 002 835 U1 discloses a plurality of agitator mechanisms for intermixing the container contents, two agitator mechanisms arranged one above the other being arranged opposite an individual agitator mechanism. For high fermentation process efficiency, as uniform a biomass distribution as possible in the fermenter liquid is considered necessary. In addition, a filling level measurement device is provided, by means of which the filling height in the container is detected and a corresponding filling level measurement signal is generated as a height actual-value signal. A filling level measurement signal is delivered to a control device which, when a lower filling height is detected, activates a height servomotor for the agitator mechanism designed as a submersible motor agitator, such that the latter is lowered and its agitating blades are thereby completely submerged even further.

The fermentation substrates used for generating biogas usually have structurally viscous flow properties. Structurally viscous means that the dynamic viscosity of the fermentation substrate decreases with an increase in shear rate. Viscosity is therefore not a value, but a function. For each induced shear rate, an associated viscosity is obtained. The viscosity in the container is consequently locally different. It depends on the shear rates present locally. The reason for this is the local velocities which influence the flow in the container.

Shear rates are generated by the movement of the propeller of an agitator mechanism. In the surroundings of the propeller, the local viscosity decreases in the case of structurally viscous fermentation substrates. With an increase in distance from the propeller, the shear rate is reduced and the viscosity rises correspondingly. The result of this is that the propeller predominantly sucks in fermentation substrate from near-propeller regions where the fermentation substrate has a low viscosity. This gives rise to near-propeller regions in which the substrate is transported at high velocities in a small volume only around the propeller itself. These near-propeller regions are designated as caverns. Where agitator mechanisms operate only locally in a cavern, optimal intermixing of the container contents does not take place because the generation of flow is restricted to these regions. Consequently, this leads to a reduction in the useful reactor volume in relation to the actual capacity of the bioreactor. As a result, less biogas and therefore also less useful methane are generated in the smaller useful reactor volume. The methane fraction or methane quantity has effects upon the economically efficient operation of a bioreactor.

SUMMARY OF THE INVENTION

It is the object of the invention to maximize the converted fermentation substrate quantity and the generated methane gas quantity. It is also sought to reduce the residence time required for biogas production and the required energy.

This object is achieved according to the invention in that the actual value of at least one measurement quantity is detected and transmitted to a regulating unit, and in the regulating unit there is stored a setpoint value, wherein the regulating unit calculates the deviation of the actual value from the setpoint value and, as a function of said deviation, varies manipulated quantities which vary the introduction of power by the agitator mechanism and/or the composition of the container contents and/or the flow behavior of the container contents.

The profitability of a biogas plant is significantly dependent on the energy consumption of the agitator mechanisms. With the method according to the invention, the hydraulic power required for optimum operation of the plant is minimized. Data from different process-monitoring sensors are detected in the regulating unit. As a regulating unit, use may be made of a programmable logic controller, for example. Depending on the programming of the regulating unit, one or more measurement quantities may be taken into consideration as reference quantities for regulating the agitator mechanism.

The regulating unit compares the measurement values with plant-specific desired values. The operationally specific desired values depend, for example, on the size of the container, on the type of agitator mechanisms and on the arrangement of the agitator mechanisms in relation to one another. They are fixed for each application.

As a function of the regulating deviation, the regulating unit varies manipulated quantities which vary the introduction of power by the agitator mechanism and/or the composition of the container contents and/or the flow behavior of the container contents. According to the invention, different process-influencing assemblies can be regulated by the regulating unit. These include preferably the agitator mechanisms, a fermenter heater, a feed system and a recirculation unit.

In a biogas plant, the generation of methane is a primary aim. In a particularly advantageous variant of the invention, the gas mass flow generated is detected as a measurement quantity and used as a reference quantity for regulating the process-influencing assemblies. A gas mass meter may be used for this purpose. If the gas quantity falls below a certain level, the regulating unit varies for example the introduction of power by the agitator mechanism.

In biogas production not only methane but also other gases such as for example carbon dioxide are produced. It is the aim to maximize the methane fraction in the gas flow generated. In one particularly advantageous embodiment of the invention, therefore, the methane gas fraction is detected as measurement data and used as a reference quantity for the regulation of the process-influencing assemblies. The methane gas fraction in the gas flow may be determined by means of analysis units. For this purpose, use is preferably made of analysis units which operate on the basis of infra-red absorption.

A further variant for regulating the process for biogas production consists in the performance data of a machine/assembly which processes the methane gas generated being taken into consideration as a measurement quantity. If the methane gas is burned in a combustion engine, the performance of said machine can be used as a reference quantity for the regulation of process-influencing assemblies.

During ongoing operation, floating layers may form as a result of adhesion of gas bubbles to structure materials of the fermentation substrate. The floating of said structure materials and the solidification thereof on the surface of the fermentation substrate have an adverse effect on the fermentation process. In particular, a gas-impermeable floating layer may form which hinders or prevents an escape of biogas. This has an adverse effect on the conversion process in the fermentation substrate.

In one particularly advantageous embodiment of the invention, the extent of a floating layer which forms on the fermentation substrate is detected as a measurement quantity. The extent of the floating layer may be determined by the height and/or the density of the floating layer. The regulating unit regulates the process-influencing assemblies as a function of the floating layer which forms on the fermentation substrate.

It has proven to be advantageous if the biogas residue potential in a fermentation residue is detected as a measurement quantity. The mass conversion which has taken place in the fermentation substrate is determined by means of a regular evaluation of the fermentation residue which is extracted continuously or cyclically from the container. If a biogas residue potential is established, said measurement data is evaluated by the regulating unit. As a function of the measurement data, the regulating unit determines the times for an activation, deactivation or cut-in of one or more agitator mechanisms. It is also additionally or alternatively possible for the operating duration of the agitator mechanisms to be varied by the regulating unit.

In one particularly preferred embodiment of the invention, the introduction of power by the agitator mechanisms is varied by means of the rotational speed of the agitator mechanisms. If the actual values of the measurement quantities deviate from their setpoint values, the regulating unit varies the rotational speed of the agitator mechanisms as a function of the regulating deviation. The introduction of power by the agitator mechanisms may also be varied in that further agitator mechanisms are cut in. The cut-in delivers an additional introduction of power.

The regulating unit can also vary manipulated quantities which vary the composition of the container contents. For this purpose, the regulating unit can increase or lower the quantity of substrates supplied. A further possibility is to vary the digestion of the fermentation substrate by the use of enzymes. Dilution of the fermentation substrate by means of liquid manure and/or recirculate and variation of the flow properties of the fermentation substrate by the addition of chemical or biological active mechanisms are also possible. In this case, even only a phased cut-in of one or more agitator mechanisms may take place, for example in the event of a temporary change in the substrate composition or the fermentation substrate composition by the routing of recirculate.

BRIEF DESCRIPTION OF THE DRAWINGS

The invention will be described in further detail hereinafter with reference to illustrative embodiments shown in the accompanying drawing figures, in which.

DETAILED DESCRIPTION OF PREFERRED EMBODIMENTS

Figure 1:
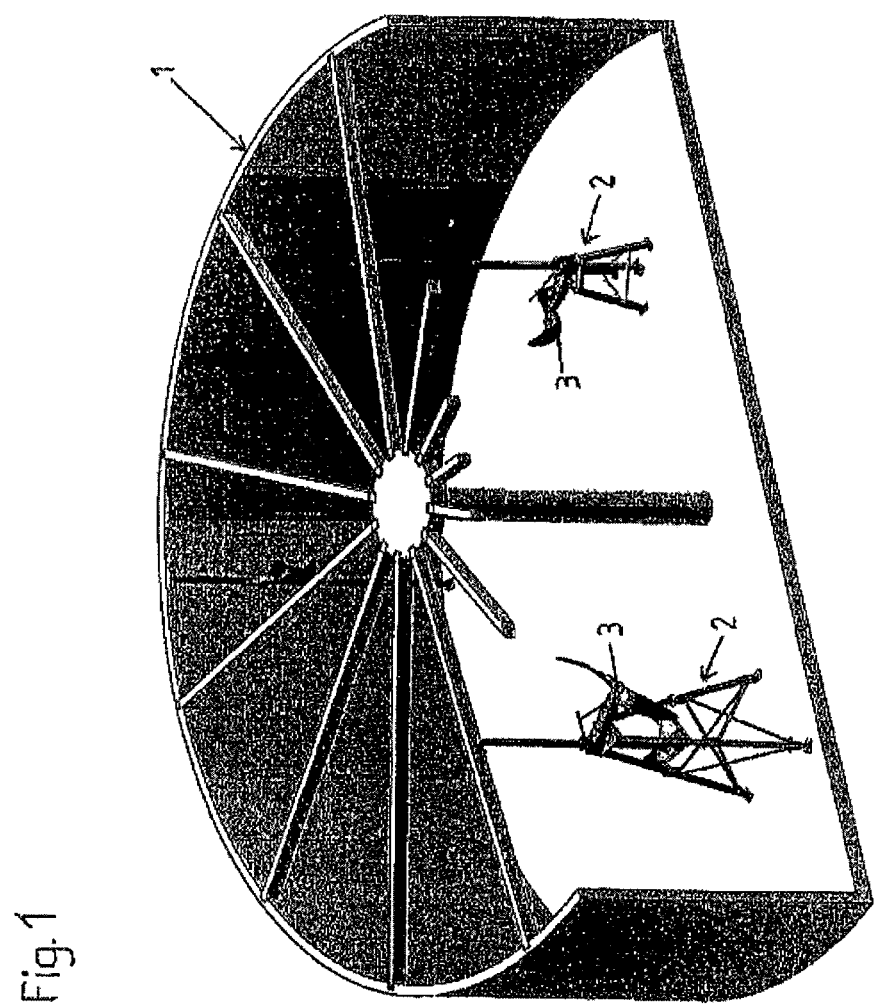
FIG. 1 shows a perspective view of a container for biogas production.

FIG. 1 illustrates a cylindrical container 1 for producing biogas. Other container forms are likewise possible. The ratio of the largest diameter to the height of the container is lower than 0.5. Positioned in the container 1 are two agitator mechanisms 2, the propellers 3 of which generate a mostly horizontal flow of the fermentation substrate in the container 1. The agitator mechanisms 2 or their propellers 3 are arranged at different heights inside the container 1. An additional agitator mechanism 11 is cut in, as required.

Figure 2:
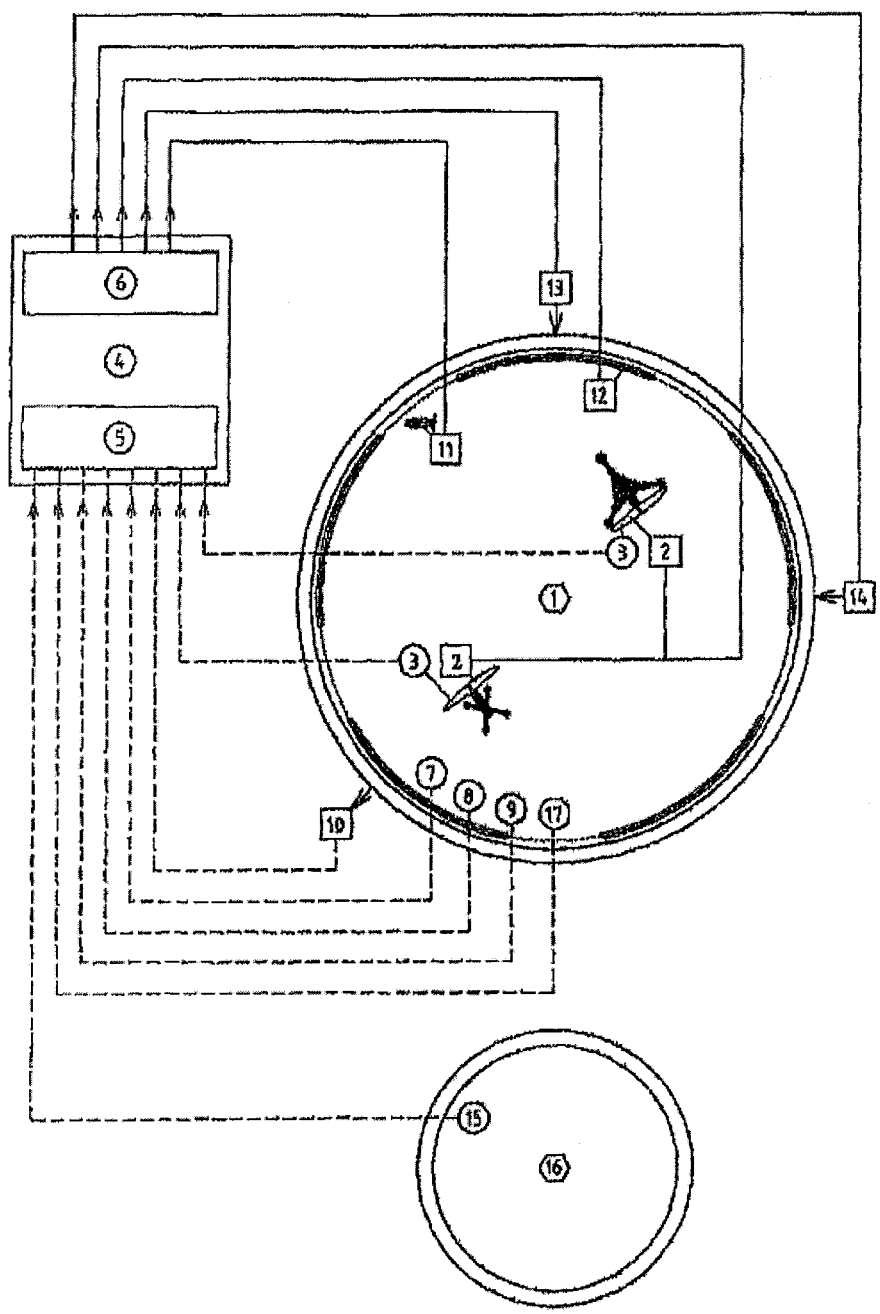
FIG. 2 shows a diagrammatic illustration of the regulation of a plant for biogas production.

FIG. 2 shows a diagrammatically illustrated regulating unit 4 for a method for producing biogas. This may be a stored-program control (SPS) or another regulating system.

The regulating unit 4 has a signal input region 5 and a signal output region 6. The signals of the data which are detected during measurements of the method are conducted to the signal input region 5. Data from various process-monitoring sensors 7, 8, 9, 10, 15, 17 and from the agitator mechanisms 2 are processed in the regulating unit 4. The signal output region 6 is operatively connected to process-influencing assemblies. Process-influencing assemblies are the agitator mechanisms 2, 11, a fermenter heating unit 12, a feed system 13 and a recirculation unit 14. These are controlled such that individual process parameters can be optimized with the aim of a maximum methane yield.

The following sensors may be used for process monitoring: at least one sensor for viscosity measurement 7, one or more sensors for flow velocity measurement 8, at least one floating layer detector 9, a gas quantity meter 10, a unit 15 for fermentation residue analysis and at least one unit 17 for determining the flow behavior of the fermentation substrate.

The sensor 7 serves for detecting the viscosity. To determine the viscosity, measurement data which are determined via the agitator mechanisms 2 may also be used. Alternatively or additionally, it is possible to employ a separate flow behavior determination unit 17. Flow behavior determination may in this case take place individually or simultaneously at a plurality of locations. The determination of the flow behavior is necessary in order to avoid too critical a flow behavior in the container 1 in terms of relevant process parameters and also damage to all the agitator mechanisms 2, 11 used in the process and to optimize their specific energy consumption. The velocity generated in the fermentation substrate is of major importance in optimizing between the gas yield and the specific energy consumption.

The sensor 8 is used for velocity measurement in the container 1. In this case, the velocity can take place at different locations by means of one or more velocity determinations.

The formation of a floating layer is monitored by means of a detector 9. Since a floating layer top has an adverse effect upon the emission of biogas from the fermentation substrate, its occurrence must be avoided or it must be destroyed as soon as possible after it has occurred. For this purpose, for example, an additional agitator mechanism 11 can be cut in and/or the rotational speed of one or more main agitator mechanisms 2 can be varied. This gives rise to flow turbulence which dissolves the floating layer.

The generated gas mass flow is detected by a gas mass meter 10. If the gas mass falls below a specific level, the regulating unit 4 adapts the introduction of power by the agitator mechanisms 2, 11. The aim of fermentation is to utilize as large an amount of the biogas potential of the substrate as possible.

The fermentation residues are collected in a fermentation residue store 16. The determination of the biogas residue potential in the fermentation residue is carried out by means of the unit 15 and is a further possible reference quantity for the regulating unit 4 and for the regulation of the agitator mechanisms 2, 11. Determination of the biogas residue potential may take place at various locations in the plant. If a specific biogas residue potential is overshot in the fermentation residue, the regulating unit 4 adapts the process-influencing assemblies 2, 11, 12, 13, 14 to the process conditions.

Basically, all the data from the signal input region 5 are processed in the regulating unit 4. The processing of the data takes place on the basis of a stored algorithm. This algorithm assumes the task of determining from the input quantities the values for controlled quantities determined from them. The controlled quantities determined are used to control the process-influencing assemblies 2, 11, 12, 13, 14 from the signal output region 6.

Signals for regulating various manipulated quantities emanate from the signal output region 6. Consequently, for example, the agitator mechanisms 2 are activated, and their rotational speed can be regulated.

In the absence of movement on the surface of the fermentation substrate, a floating layer may be formed. Moreover, the absence of movement may cause the substrate or fermentation substrate to be fed in to be distributed only insufficiently in the container 1.

When new substrate is supplied or if a floating layer has occurred, an additional agitator mechanism 11 can be cut in or regulated. The heating unit 12 supplies heat to the container 1 when new substrate is being fed in. The substrate is supplied by the feed system 13. The fodder quantity can consequently be adapted to the process parameters. Overfodder of the container 1 with substrate would have an adverse effect upon the flow behavior in the container 1 and therefore on methane production. If the flow behavior changes adversely, the fodder quantity is reduced and/or other controlled quantities, such as, for example, the velocity or recirculate quantity, is/are varied.

If fodder quantities are too low, insufficient substrate is available for methane formation. With the aid of a gas mass meter 10 and/or an analysis of the biogas residue potential in the fermentation residue, this state is detected and foddering with substrate is induced. The method has a recirculation unit 14 by means of which it is possible to add recirculate in a metered manner. A higher substrate turnover and an increased biogas yield are thereby achieved.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method for producing biogas from organic substances in a biogas generating system which includes a regulating unit and a fermenter container having a height to diameter ratio lower than 0.5 arranged to receive substrate being supplied to the container by a feed system, there being arranged in the container at least one agitator mechanism arranged to generate a horizontal flow of the organic substances in the container, the method including detecting an actual value of at least one measurement quantity indicative of a dynamic viscosity of the substrate at the at least one agitator mechanism, transmitting the actual value detected at least one measurement quantity to a regulating unit in which there is stored a setpoint value indicative of a reference substrate viscosity that is a function of at least one of a size of the container, a type of the at least one agitator mechanism and a position of the at least one agitator mechanism in the container, calculating with the regulating unit a deviation of the actual value from the setpoint value and, as a function of said deviation, increasing the dynamic viscosity of the substrate in the container by controlling at least one of an amount of power introduced to the substrate in the container by the at least one agitator mechanism, a composition of the substrate in the container, a composition of the substrate being fed into the container, and amount of substrate being at least one of added to and recirculated into the container, and a flow behavior of the container contents, the flow behavior being varied by addition of at least one of a chemical and a biologically-active mechanism to the substrate.

2. The method as claimed in claim 1, wherein the gas mass flow generated is detected as an additional measurement quantity.

3. The method as claimed in claim 1, wherein the methane gas fraction is detected as an additional measurement quantity.

4. The method as claimed in claim 1, wherein performance data of a machine/assembly which processes the biogas are detected as an additional measurement quantity.

5. The method as claimed in claim 1, wherein the extent of a floating layer which forms is detected as an additional measurement quantity.

6. The method as claimed in claim 1, wherein the biogas residue potential in a fermentation residue is detected as an additional measurement quantity.

7. The method as claimed in claim 1, wherein the regulating unit varies the rotational speed of the agitator mechanism.

8. The method as claimed in claim 1, wherein the regulating unit actuates at least one additional agitator mechanism.

9. An apparatus for producing biogas from organic substances, said apparatus comprising:
    a container having a height to diameter ratio of 0.5;
    a feed system configured to supply fermentation substrate to said container;
    at least one agitator mechanism arranged to generate a horizontal flow of the organic substances in said container;
    a measurement device for measuring a quantity indicative of a dynamic viscosity of the fermentation substrate in the container at the at least one agitator mechanism; and
    a regulating unit configured to receive from said measurement device the measured value of the quantity indicative of a dynamic viscosity of the fermentation substrate at the at least one agitator mechanism and having stored therein, a setpoint value of a quantity indicative of a reference substrate viscosity that depends on at least one of a size of the container, a type of the at least one agitator mechanism and position of the at least one agitator mechanism in the container;
    wherein said regulating unit is configured to calculate a deviation of the measured value of said at least one quantity indicative of the dynamic substrate viscosity at the at least one agitator from the setpoint value and of the quantity indicative of the reference substrate viscosity, control as a function of said deviation an increase in the dynamic viscosity of the substrate at the at least one agitator mechanism of at least one of an amount of power being introduced to the substrate in the container by the at least one agitator mechanism, a composition of the substrate in the container, a composition of the substrate being fed into the container, and amount of substrate being at least one of added to and recirculated into the container, and a flow behavior of the container contents, the flow behavior being varied by addition of at least one of a chemical and a biologically-active mechanism to the substrate.

10. The apparatus as claimed in claim 9, wherein a gas mass flow generated in the apparatus is detected as a measurement quantity.

11. The apparatus as claimed in claim 9, wherein the methane gas fraction of a gas generated in the apparatus is detected as a measurement quantity.

12. The apparatus as claimed in claim 9, wherein performance data of a machine/assembly which processes biogas generated in the apparatus are detected as a measurement quantity.

13. The apparatus as claimed in claim 9, wherein the extent of a floating layer which forms in the container is detected as a measurement quantity.

14. The apparatus as claimed in claim 9, wherein the biogas residue potential of a fermentation residue in the container is detected as a measurement quantity.

15. The apparatus as claimed in claim 9, wherein the regulating unit varies the rotational speed of the agitator mechanism.

16. he apparatus as claimed in claim 9, wherein the regulating unit actuates at least one additional agitator mechanism.

* * * * *